United States Patent [19]
Freller

[11] 4,382,784
[45] May 10, 1983

[54] CUSTOM DENTAL SHADE GUIDE SELECTOR AND METHOD FOR ITS USE

[76] Inventor: Robert T. Freller, 110 Chipwood Crescent, Willowdale, Ontario, Canada, M2J 3X7

[21] Appl. No.: 164,542

[22] Filed: Jul. 2, 1980

[51] Int. Cl.³ .............................................. A61C 19/10
[52] U.S. Cl. ........................................ 433/26; 433/141
[58] Field of Search ...................... 433/26, 163, 34, 40, 433/45, 208, 219; 206/83; 264/19, 20

[56] References Cited

U.S. PATENT DOCUMENTS

| | | | |
|---|---|---|---|
| 362,803 | 5/1887 | White | 433/26 |
| 1,335,681 | 3/1920 | Goodwin | 433/208 |
| 1,382,010 | 6/1921 | Nishi | 264/19 |
| 1,518,608 | 12/1924 | Short | 433/26 |
| 1,634,687 | 7/1927 | Sanders | 206/83 |
| 1,704,723 | 3/1929 | Charen | 206/83 |
| 2,249,634 | 7/1941 | Myerson | 433/26 |
| 2,262,641 | 11/1941 | Hayward | 433/26 |
| 2,706,854 | 4/1955 | Skinner | 433/219 |
| 2,756,504 | 7/1956 | Levine | 433/26 |

FOREIGN PATENT DOCUMENTS

| | | | |
|---|---|---|---|
| 1491108 | 7/1969 | Fed. Rep. of Germany | 433/26 |
| 2641740 | 3/1978 | Fed. Rep. of Germany | 433/26 |
| 15762 | of 1902 | United Kingdom | 433/40 |
| 226794 | 4/1925 | United Kingdom | 206/83 |
| 379485 | 9/1932 | United Kingdom | 433/219 |

*Primary Examiner*—Gene Mancene
*Assistant Examiner*—John J. Wilson
*Attorney, Agent, or Firm*—Jerome Goldberg

[57] ABSTRACT

A dental shade guide selector including a color tooth sample, a handle for manipulating the sample in the mouth and a holder for storing the color tooth samples. The color tooth sample includes a frame having a base plate and a rim bordering the plate. A layer of porcelain or the like is fused or otherwise fixidly attached on the plate inside the border of the rim. The plate has a front convex surface and a rear concave surface. The rim has a greater height at the incisor end of the tooth sample than at the gingival end of the tooth sample, so that the porcelain layer is thicker at the incisor end than at the gingival end. A pair of spaced apart feet extend outward from the rear surface of the plate to define a channel (curved) therebetween for receiving the support of the artificial tooth positioned in the mouth. The method for using the tooth sample comprises the obtaining of a first batch of said porcelain to simulate a first color, and constructing therefrom a first color sample, for matching the color of real teeth, and using said first batch to construct artificial teeth having said first color, and discarding said first color sample when said first batch of porcelain is depleted. A second batch of said porcelain simulating said first color is obtained and a second color sample is constructed from said second batch, and using the second batch to construct artificial teeth having said first color.

20 Claims, 20 Drawing Figures

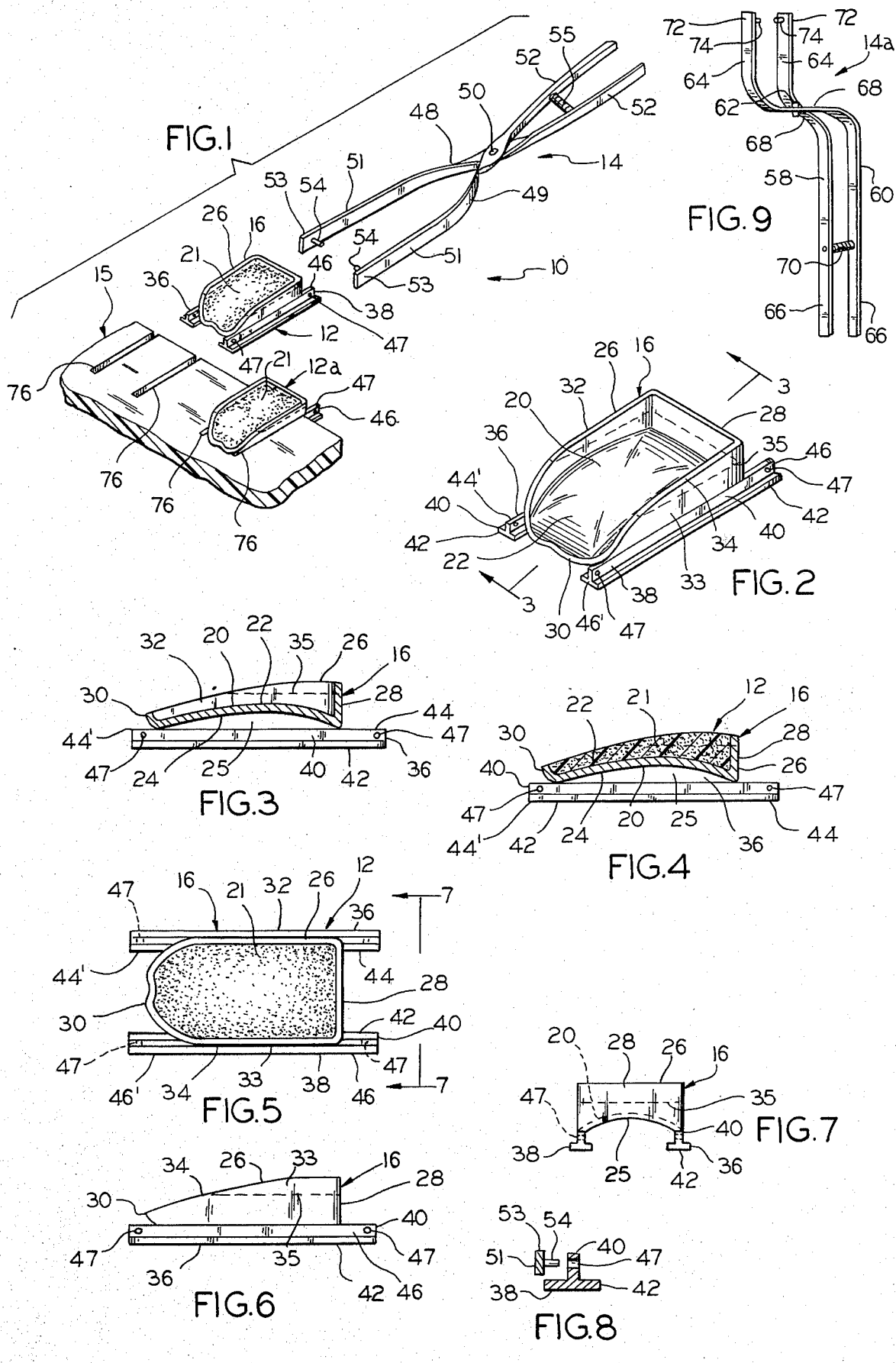

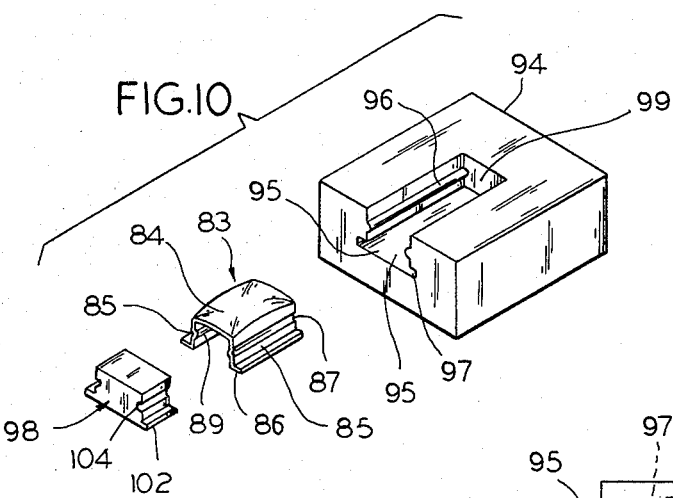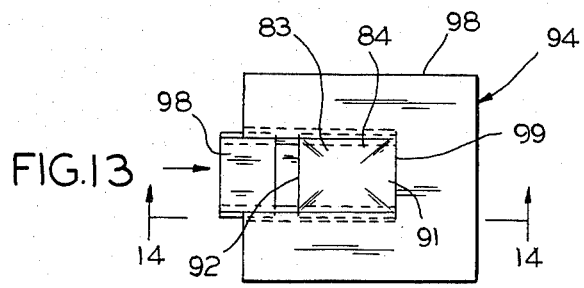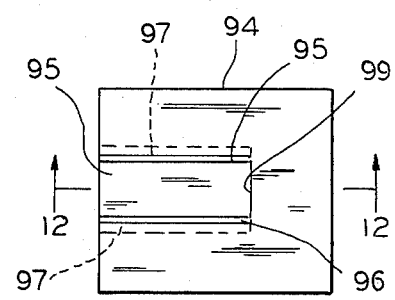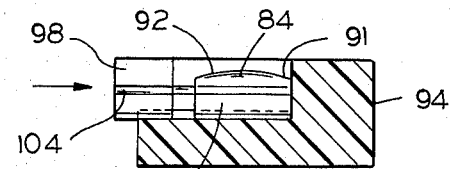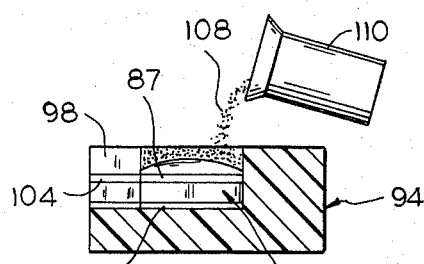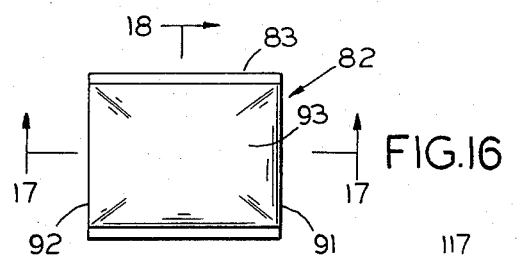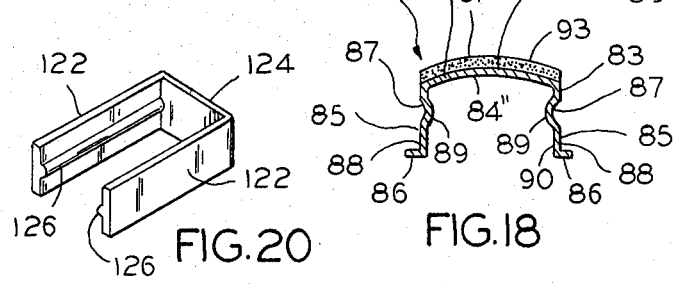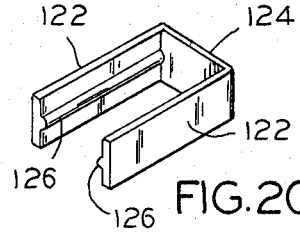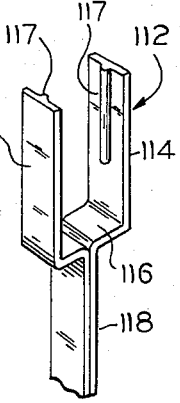

CUSTOM DENTAL SHADE GUIDE SELECTOR AND METHOD FOR ITS USE

BACKGROUND OF THE INVENTION

This invention relates generally to a dental shade selector for matching the color of the porcelain veneer of the artificial or prepared tooth or bridgework with the patient's natural teeth, and more specifically relates to a color shade selector and method which more accurately matches the color of the prepared tooth with the adjacent real teeth.

Dental bridgework or crowns generally comprise a rigid supporting frame of a suitable material such as a gold or other alloy on which a porcelain material is fused. The proper color or shade for the porcelain is essential for simulating the prepared tooth with the patient's real teeth. In selecting the correct color for the prepared tooth, the dentist commonly utilizes a color shade guide which includes a plurality of color samples to provide graduating shade variations, for approximating the color match. Generally, these prior guides did not have a metal backing nor did they have similar thickness for the porcelain veneer as the constructed crown or bridge. Therefore, when the selected material from the guide samples originally resembling the natural teeth, was applied to the artificial tooth or bridgework, there was a noticeable variance of color between the completed prepared tooth and the natural teeth.

Some previously disclosed color selectors comprised samples of teeth having a metal or plastic base and a veneer of porcelain. The metal or plastic backing of these samples were not similar in color to the supporting structure of the artificial tooth, and consequently, an accurate reproducible match was not achieved.

The previously used dental color samples did not vary in the thickness of the porcelain veneer spread over or affixed on the body of the sample. Therefore, although the selected color or shade may have been accurate for the outer end of a front tooth, for example, it quite often would be in variance with adjacent teeth in the area of the tooth near the gum line.

In using the prior shade guides, the dentist selected the sample that most closely resembled the color or shade of the teeth adjacent to the fabricated crown. Then the bridgework or crown was constructed using the same porcelain substance for the outer veneer as the selected sample. Usually, the previously used shade guide selectors were provided by a manufacturer. Frequently, the color shade of the fabricated tooth was appreciably different from the selected sample, and consequently, such prior shade guides were not capable of providing reproducible accurate shade variations, eventhough the matching may have been accurate with the selected samples.

The aforedescribed undesirable effect is primarily attributable to the color shade differences between batches of the same color shade compound. Thus, a color difference existed between the color samples and the batch used by the dental laboratory to simulate the artificial tooth with the sample. The color differences have been found to be even more severe when the sample for the shade guide selector is constructed by one manufacturer and the corresponding color shade compound used to simulate the selected sample is provided by another manufacturer.

Furthermore, the dental laboratory may not even have the compound available for matching the dentist's selected sample from another manufacturer's shade guide. In this situation, the dental laboratory would be required to derive the proper shade compound by mixing the constituent parts of the compound and try-fire the compound. Generally, preliminary tooth constructions would be necessary before obtaining even a minimal acceptable color match of the dentist's shade selection.

The dentist in his effort to customize or precisely match the selected sample with the patient's real teeth, may often apply a stain to the selected sample. Since the porcelain veneer of the sample didn't match with the corresponding porcelain compound used for simulating the sample, the stain applied by the dentist further complicated the matching procedure. The subject invention, on the other hand, enables the dental laboratory to easily and accurately customize the staining requirements of the dentist, and precisely reproduce the desired shading on the artificial tooth.

It is, therefore, a primary object of the subject invention to provide a shade selector for accurately matching the fabricated bridgework with the patient's adjacent real teeth.

It is another primary object to provide a method for accurately matching the fabricated bridgework with real teeth.

Another object is to provide a shade selector comprising a plurality of samples corresponding to a graduation of color variations and a detachable handle which is easy to manipulate, for positioning the individual tooth samples in the mouth to select the closest sample to the shade of the real adjacent teeth.

A primary feature of the invention is to use material from the same batch of the material to form the color shade tooth sample and also to form the color simulated artificial tooth.

Another primary feature is to provide a color tooth sample having a frame constructed to approximate the average amount of porcelain reduction during baking, so as to provide an average build up of porcelain, to simulate the thickness for the final restoration.

Another feature is to provide color tooth samples, for varying the color shades both at the outer end of the tooth and adjacent the gum line.

Another feature of the subject invention is to provide a backing, which is constructed from one of the actual metals used as understructure in the production of crowns and bridges.

Still another feature is that the dentist is provided with a tooth button sample which can be stained by him, to customize the shade selection; and, thereafter, the stain can be removed and the tooth button may again be used. (The stain the dentist uses is communicated to the dental laboratory, and easily and exactly reproduced and baked or fired to the porcelain.)

SUMMARY OF INVENTION

The custom dental shade guide selector includes a color/shade tooth sample comprising a frame having an outer rim, for containing a layer of porcelain. The outer rim has greater height at the outer or incisor end of the tooth sample than at the inner or gingival end of the tooth sample. A pair of feet extend outward from the back side of the frame to define a channel therebetween. The feet also extend outward from the incisor and gingival ends of the tooth sample to afford gripping areas for a pair of tongs, used for positioning the tooth sample in the desired location inside the mouth. The feet of the tooth sample are insertible in a holder for storing the tooth samples.

The method for matching the color of the artificial tooth with the adjacent real teeth comprises the steps of: preparing or obtaining a batch of a first tooth color simulating compound such as a porcelain compound to simulate a first color or shade of real teeth, and constructing therefrom a first tooth color sample and utilizing such compound and said sample for providing an artificial tooth having a color to simulate said first color, and discarding the color sample when said first batch of compound is depleted, and constructing a second tooth sample of said first color or shade when a second batch of said tooth color compound is prepared or obtained for constructing artificial teeth having said first color.

BRIEF DESCRIPTION OF THE DRAWINGS

Referring now to the drawings, in which the same characters of reference are employed to indicate corresponding similar parts throughout the several Figures of the Drawings:

FIG. 1 is a perspective view of the dental shade guide selector, including the sample tooth, gripping tongs and holder for the sample teeth;

FIG. 2 is a perspective view of the frame for the sample tooth;

FIG. 3 is a cross-sectional view of the frame of the tooth sample, taken on the plane of the line 3—3 in FIG. 2;

FIG. 4 is a similar cross-sectional view as FIG. 3, but illustrating the tooth sample including the outer porcelain veneer;

FIG. 5 is a top view of the tooth sample;

FIG. 6 is a side view of the tooth sample;

FIG. 7 is an outer or incisor end view as viewed from the plane of the line 7—7 of FIG. 5;

FIG. 8 is a fragmentary sectional view to illustrate one of the prongs of the gripping tongs spaced from the receiving opening formed in the tooth sample; and FIG. 9 illustrates a modified gripping means, which is bent to be manipulated from a position below the chin of the patient.

FIG. 10 illustrates a perspective view of the tooth sample frame and mold parts spaced apart for forming the tooth shade sample, and embodying the principals of the invention;

FIG. 11 is a top view of the mold holder in FIG. 10;

FIG. 12 is a sectional view taken on the plane of the line 12—12 in FIG. 11 and viewed in the direction indicated;

FIG. 13 is a top view of the tooth sample frame positioned in the assembled mold parts;

FIG. 14 is a side sectional view to illustrate the tooth sample frame inside the mold holder and showing the mold support member being inserted inside the mold holder;

FIG. 15 is a sectional view similar to FIG. 14 but illustrating the support member operatively abutting the tooth sample frame;

FIG. 16 is a top view of a tooth shade sample;

FIG. 17 is a side sectional view of the tooth shade sample taken on the plane of the line 17—17 in FIG. 16 and viewed in the direction indicated;

FIG. 18 is an edge sectional view of the tooth shade sample taken on the plane of the line 18—18 in FIG. 16, and viewed in the direction indicated;

FIG. 19 is a perspective view of a holder for positioning the tooth shade sample; and FIG. 20 is another embodiment of a mold holder for forming the tooth shade sample.

DESCRIPTION OF THE PREFERRED EMBODIMENT

Referring now to FIG. 1 of the drawing, the reference numeral 10 indicates generally a dental shade selector which includes a tooth sample 12 for matching shades or colors of the dental patient's real teeth, gripping tongs 14 for inserting the color sample 12 inside the patient's mouth, a holder 15 for storing the tooth samples 12. The tooth sample shown positioned inside the holder 15 represents a different tooth shade or color and is identified by the same numeral 12 and a suffix "a".

The tooth sample 12 comprises a frame 16 having a base plate 20 on which a color matching layer 21 is fused or otherwise rigidly attached. The front surface 22 of the base plate 20 is convex shaped, and the rear surface 24 thereof is concave shaped to provide an arcuate cavity 25 to receive the metal support (under structure) of the crown or artificial tooth when the tooth sample 12 is positioned in the mouth (see FIGS. 3, 4 and 7). The base plate 20 is constructed from a metal material which has substantially the same color as the metal support for the crown or bridgework to be secured inside the mouth.

A rim 26 extends upward from the peripheral edge of the front surface 22 of the base plate 20 and is integrally formed thereto. The rim 26 includes an incisor end 28 and a gingival end 30 and sides 32, 33. As may be seen from FIGS. 2 and 3 of the drawing, the height of rim 26 from the outer or forward edge 34 inward to the base plate 20, decreases from the incisor end 28 to the gingival end 30.

The rim 26 is constructed from a thin pliable material which is easily bent and broken away from the base plate 20, after the tooth sample has been fabricated. The rim 26 is perforated along the line 35, to facilitate the removal of the rim 26.

A pair of feet 36,38 are attached to the sides 32,33 respectively of the frame 16. Each foot 36,38 comprises a neck portion 40 and a bar portion 42 integrally formed together, so that the cross sectional area of the feet 36,38 is an inverted "T", as may be seen from FIGS. 7 an 8.

The color matching layer 21 is constructed from a porcelain compound which is inserted in the frame 16 in the space defined inside the rim 26. The quantity of porcelain is just sufficient to extend beyond the forward edge 34 of the rim 26, so that the color matching layer 21 is substantially level with the outer edge of the rim 26 after the porcelain has been sufficiently baked. The baking process also rigidly attaches the color layer 21 to the front surface 22 of the base plate 21. The color matching layer 21 has an average build up or thickness of porcelain to simulate the real tooth.

The outer parts 44,46 respectively of the feet 36,38 extend outward from the incisor end of the tooth sample 12. The opposite outer parts 44', 46' of the feet 36,38 extend outward from the gingival end of the tooth sample 12. Each of the outer parts 44,44', 46 and 46' include openings 47 formed therein.

Turning now again to FIG. 1, the tongs 14 include tong members 48,49 pivotally attached to each other by pin 50. Each tong member 48,49 includes a finger portion 51 and a handle portion 52. The outer tip 53 of each of the finger portions 51 include a prong 54 facing inward toward the other prong 54, for inserting into the openings 47 in the outer parts 44,44', 46 and 46' of the feet 36,38.

The fingers 51 are normally in a retracted spaced apart condition due to the spring 55 attached to and between the handles 52. Forcing the handles 52 farther apart against the resilient force of spring 55, in turn, spreads the tips 53 of the fingers 51 farther apart.

To insert the prongs into the openings 47, the handles 52 are spread further apart, and thereafter positioned into two opposed openings 47. The prongs 54 are locked in place inside the openings 47, by the resilient action of the spring 55, urging the fingers 51 toward each other.

In FIG. 9, alternative gripping tongs identified by the designation 14a, is illustrated. The tongs 14a include tong members 58,60 which are pivotally attached to each other by pin 62. Each tong member 58,60 includes a finger portion 64, a handle portion 66 and a substantially perpendicular intermediate portion 68 integrally formed to the finger and handle portions 64,66. The tong members 58,60 are also normally in a retracted and spaced apart condition due to spring 70.

The intermediate portions 68 cause the handle portions 66 to extend downward and the finger portions 64 to extend upward, as viewed from FIG. 9. In this manner, any shadow, however slight, from the dentist's hand is avoided, and thereby ensuring an optimum match between the tooth sample 12 and the adjacent real teeth of the patient.

The outer tips 72 of each of the fingers 64 of tong 14a include prongs 74 for inserting into the openings 47. The prongs 74 are locked in place inside the openings 47 by the resilient action of spring 70.

The tooth samples 12, 12a etc. are stored in the holder 15. As may be seen from FIG. 1, the tooth samples 12 slide into and out from a pair of elongated pathways 76 notched out from the holder 15. Each pathway 76 has an inverted "T" cross section dimensioned to receive the feet 36,38 of the tooth sample 12. The outer parts 44,46 of the feet 36,38 protrude out from the holder 15, to permit ease of withdrawing and reinserting the sample 12 into the holder 15.

The dental laboratory obtains or prepares a first batch of a procelain compound to simulate a first color or shade of real teeth. From this batch of the porcelain compound the dental laboratory constructs a plurality of tooth samples 12, one sample 12 to be supplied to each of the dentists serviced by the dental laboratory.

A second batch of a porcelain compound is obtained or prepared to simulate a second color or shade of real teeth. From this second batch of porcelain compound, the dental laboratory constructs another plurality of tooth samples 12a, one sample 12a to be supplied to each of the dentists serviced by the laboratory.

Similarly, the dental laboratory obtains and prepares additional batches of a porcelain compound to simulate other colors or shades of real teeth. From each of these additional batches of porcelain compounds, tooth samples are constructed representing different colors or shades of real teeth, and each such different colored sample tooth is supplied to each of the dentists serviced by the dental laboratory.

When the dentist selects a tooth sample simulating the patient's adjacent real teeth, the dental laboratory constructs the artificial tooth or crown from the exact batch of porcelain from which the selected sample was prepared. In the event, the dentist selects a specific sample but desires a slightly altered shade, the dental laboratory utilizes the same batch of porcelain compound as the selected tooth sample was constructed from, to fabricate the porcelain veneer having the slightly altered color as the selected sample tooth.

Furthermore, the dentist may select a specific sample simulating the adjacent real teeth and apply a darkening stain thereto. The dental laboratory would construct the porcelain veneer for the artificial tooth or crown utilizing the same batch as used to construct the sample tooth. The same type of stain used or communicated by the dentist is applied by the dental laboratory onto the porcelain veneer and baked therein to provide the desired artificial tooth coloring.

When a batch of the compound, for example, the first batch is depleted, the dental laboratory obtains or prepares another batch of the same compound, and from this batch the dental laboratory constructs another plurality of tooth samples 12 to be supplied to each of the dentists serviced by the laboratory, and instructs the dentists to return or discard the previously constructed tooth samples 12.

In the method herein for simulating teeth colors, the dental laboratory is able to accurately simulate the color or shade of the selected sample from the same batch of compound used to construct the porcelain layer 21 of the tooth sample 12, 12a etc.

Moreover, the laboratory is also able to accurately vary the color of the tooth by utilizing "modifiers" or adding stain to the material of the compound, since the base compound used to construct the color tooth sample may be precisely reproduced.

In addition to storing the base porcelain compounds used to fabricate both the tooth sample 12 and the artificial tooth or crown, the tooth sample 12 provided by the dental laboratory is similar in other respects to the artificial tooth or crown. The base plate 20 of the frame 16 is substantially the same color as the support structure of the artificial tooth. The thickness of the color sample is also substantially the same as the artificial tooth, both at the incisor and gingival end of the tooth. The average thickness for the artificial tooth is easily achieved by filling the frame 16 with the porcelain compound within the boundary defined by the rim 26.

Referring now to FIGS. 10 through 19, another embodiment of the subject invention will be described. As shown in FIG. 18, a tooth shade sample 82 comprises a frame 83 including a base plate 84 having a convex outer surface 84' and a concave inner surface 84". A pair of spaced apart legs 85 extend outward from the base plate 84. A flange 86 is bent outward from the free ends of each of the legs 85.

An elongated concaved groove 87 is formed on the outside surface 88 of each foot 86. An elongated convex hump 89 protrudes from the inside surface 90 of each leg 85 and is directly opposed to notch 87. The frame 83 is more convex at the incisor end 91 than at the gingival end 92.

The color matching layer 93 is fused or otherwise rigidly attached to the base plate 84, and is constructed from a procelain or similar type material. The frame 83 is a metal material.

A mold holder 94 is used to easily and accurately fabricate the color matching layer 93 on the base plate 84. The mold holder 94 may be constructed from a plastic such as a plexiglas or other suitable material. A cavity 95 is formed in the holder 94 defined in part by opposed side walls 95', with each side wall 95' having an elongated bump 96 protruding inward therefrom to be received in the groove 87 of the frame 83 of the tooth shade sample 82.

The cavity 95 includes a pair of opposed elongated notches 97 to receive the flanges 86 of the frame 83 of the tooth sample 82.

Thus the frame 83 is inserted in the cavity 95, the bumps 96 received in the grooves 87 of the frame 83, and the flanges 86 received in the grooves 97.

A support member 98 similarly constructed as the outer side configuration of the frame 83 is also positioned in the mold holder 94 to securely sandwich the frame 83 between the support member 98 and the end wall 99. The support member 98 includes a pair of outward protruding feet 102 for sliding into the notches 97, and a pair of depressions 104 to receive the bumps 96 of the mold holder 94. The height of the support member 98 is greater than the frame 83 and is substantially flush with the outer edges of the side walls 95'. The inner end 106 of the support member is opposed to the end wall 99.

Referring now specifically to FIG. 15, it will be seen that a powder porcelain substance 108 may be poured from a container 110 into the mold arrangement bounded at the bottom by the plate 84 of the frame 83 and at the sides by the side walls 95' and the end wall 99 of the mold holder 94 and the inner end 106 of the support member 98. The outer or upper edges of the sidewalls 95', the end wall 99 and the inner end 106 extend above the plate 89 of the frame 83. The porcelain powder 108 is poured to a level just below the outer edges of the mold arrangement. The mold holder 94 with the layer of porcelain 108 spread over the plate 84 of the frame 83 is placed into an over for firing the porcelain to fuse the porcelain to the metallic frame 83. During the firing process, the porcelain layer expands to the outer edges of the sidewalls 95', end wall 99 and inner end 106.

Turning now to FIG. 19, a tooth shade sample holder indicated generally by the reference numeral 112 is illustrated and comprises a pair of resilient arms 114 with a web 116 connecting the bottom or inner ends of the arms 114 together. A hump 117 protrudes inward from the inside surface of each of the arms 114 to extend into the grooves 87 of the frame 83 of the tooth shade sample 82. a handle 118 is integrally attached to the web 116. The handle 118 could also be bent in the manner that the gripping tongs 14a are bent as shown in FIG. 9. To insert the tooth shade sample, the arms 114 are spread apart and the tooth shade sample 82 is placed therebetween so that the humps 117 are received in the grooves 87, and the release of the arms 114 resiliently secures the humps 118 into the grooves 87.

Referring to FIG. 20, another embodiment for a mold holder indicated generally by the reference numeral 120 is illustrated, and is constructed in a substantially "U" shape. The mold holder 120 comprises a pair of resilient side bars 122 integrally connected together by a web 124. The bars 122 each includes an elongated hump 126 to extend into the grooves 87 of the frame 83. To insert the tooth sample 82, the side bars 122 are spread apart and the tooth sample inserted therebetween so that upon release of the bars 122, the humps resiliently lock into the grooves 87 of the frame 83.

The mold holder 120 may be bent into the desired shape from a sample strip of material. The sample holder 112 (FIG. 19) may be formed from two strips of material. A pliable metal material such as aluminum or other suitable material may be used.

The description of the preferred embodiment of this invention is intended merely as illustrative of the subject invention, the scope and limits of which are set forth in the following claims:

I claim:

1. A dental shade guide selector including a sample tooth having a specific shade or color for matching with the color or shade of real teeth for providing the color or shade for an artifical crown or tooth having a support structure and a veneer of porcelain or the like, said sample tooth comprising a frame having:
    a body portion having a front surface and a rear surface, an incisor end and a gingival end for positioning adjacent the gum line of the patient when matching the color of the sample tooth with the color of adjacent real teeth;
    a rim extending outward from the periphery edge of the front surface of the body portion;
    a layer of porcelain affixidly attached to the body portion and confined within the area bordered by said rim;
    a pair of spaced apart feet attached to the rear surface for defining a channel therebetween for receiving the support structure of said artificial tooth inside the patient's mouth, the outer parts of said feet extending outward from the incisor end of the body portion; and
    a pair of tongs for gripping said outer parts of said feet.

2. A dental shade guide selector including a sample tooth having a specific shade or color for matching with the color or shade of real teeth for providing the color or shade for an artificial crown or tooth having a support structure and a veneer of porcelain or the like, said sample tooth comprising a frame having:
    a body portion having a front surface and a rear surface, an incisor end and a gingival end for positioning adjacent the gum line of the patient when matching the color of the sample tooth with the color of adjacent real teeth;
    a rim extending outward from the periphery edge of the front surface of the body portion;
    a layer of porcelain affixidly attached to the body portion and confined within the area bordered by said rim; and
    a pair of spaced apart feet attached to the rear surface for defining a channel therebetween for receiving the support structure of said artificial tooth inside the patient's mouth, the cross-sectional area of each of said feet being substantially an inverted "T" shape incuding a bottom bar and a forward extending neck for attachment at the forward end thereof to the rear surface of the body portion.

3. The dental selector of claim 2, further includes:
    a holder having a pair of spaced apart openings to receive said feet for storing said sample tooth, the cross-sectional area of each of said openings is substantially an inverted "T" shape including a bottom portion and an upward extending portion for receiving respectively said bottom bar and said neck of said foot.

4. A dental shade guide selector including a sample tooth having a specific shade or color for matching with the color or shade of real teeth for providing a support structure and a veneer of porcelain or the like, said sample tooth comprising:

a body portion having a front surface, a rear surface, an incisor end, and a gingival end for positioning adjacent the gum line of the patient when matching the color of the sample tooth with the color of adjacent real teeth;
a rim extending outward from the periphery of the front surface of the body portion;
a pair of spaced apart feet attached to the rear surface for defining a channel therebetween for receiving the support structure of said artificial tooth inside the patient's mouth; and
a pair of tongs for gripping said outer parts of said feet, each of the outer parts of said feet at least at one end of said body portion including openings, and said tongs including a pair of tong members and each of the tong members including prongs for positioning in said openings.

5. The dental shade guide selector of claim 4, wherein the outer parts of said feet at the gingival end of the body portion include openings for receiving said prongs.

6. The dental shade guide of claim 4, wherein said tongs include a resilient means for resiliently securing the prongs inside said openings.

7. The dental shade guide selector of claim 4, wherein each of said tong members include a finger portion having one of said prongs, a handle portion and an intermediate portion substantially perpendicular to said finger and handle portions.

8. A dental shade guide selector including a sample tooth having a specific shade or color for matching with the color or shade of real teeth for providing the color or shade for an artificial crown or tooth having a support structure and a veneer of porcelain or the like, said sample tooth comprising a frame having:
a body portion having a front surface and a rear surface, an incisor end and a gingival end for positioning adjacent the gum line of the patient when matching the color of the sample tooth with the color of adjacent real teeth;
a rim extending outward from the periphery edge of the front surface of the body portion;
a layer of porcelain affixidly attached to the body portion and confined within the area bordered by said rim;
a pair of spaced apart feet attached to the rear surface for defining a channel therebetween for receiving the support structure of said artificial tooth inside the patient's mouth; and
a holder having a pair of pathways formed therein, to receive said feet of the sample tooth, for storing said sample tooth, each of said feet including a bar portion and a neck portion, said neck portion being attached to the rear side of the body portion, the cross-sectional area of each of said feet taken on a plane passing through said bar portion being substantially an inverted "T", and the cross-sectional area of said pathway also being substantially an inverted "T" to receive said feet.

9. A dental shade guide selector including a sample tooth having a specific shade or color for matching with the color or shade of real teeth for providing the color or shade of real teeth for providing the color or shade for an artificial crown or tooth having a support structure and a veneer of porcelain or the like, said sample tooth comprising a frame having:
a body portion having a front surface and a rear surface, an incisor end and a gingival end for positioning adjacent the gum line of the patient when matching the color of the sample tooth with the color of adjacent real teeth;
a rim extending outward from the periphery edge of the front surface of the body portion;
a layer of porcelain affixidly attached to the body portion and confined within the area bordered by said rim, said rim being formed from a pliable material to enable said rim to be removed after said layer is fixidly attached to the body portion.

10. The dental shade guide selector of claim 9, wherein said rim is perforated inward from the outer edge thereof.

11. A method for reproducing a color shade of teeth for an artificial tooth from a sample tooth constructed from a frame having a base plate and a removable rim, comprising the steps of:
preparing a batch of a compound for forming the porcelain veneer of a sample tooth corresponding to a color shade;
taking a first portion of said batch and applying it on said base plate within the area defined by said rim;
securing said first portion on said base plate of the frame;
removing said rim after said first portion is secured on said base plate;
taking a second portion of said batch and applying it on a backing of the artificial tooth; and
securing said second portion of said batch on said backing of the artificial tooth to provide said color shade on said artificial tooth.

12. In a dental shade guide selector including a sample tooth, a mold holder, and a tooth sample gripping means, said sample tooth including a frame comprising:
a base plate having a front surface and a rear surface, an incisor end and a gingival end for positioning adjacent the gum line;
a pair of spaced apart feet attached to the base plate for defining a channel therebetween for receiving the support structure of an artificial tooth inside the patient's mouth; and
securing means for associating the sample tooth with the mold holder and the gripping means.

13. The shade guide selector of claim 12, wherein said mold holder and gripping means includes cooperative securing means for attaching with said securing means of said sample tooth, one of said securing means includes a depression and the other said securing means includes a hump for extending into said depression.

14. The sample tooth of claim 12 includes:
a flange extending outward from each of the feet of the frame; and
a pair of notches are formed in the mold holder to receive said flanges.

15. The mold holder of claim 12 includes:
a cavity to receive the frame of said tooth sample, said cavity being defined by a pair of side walls and a rear wall, the side of the mold holder opposite said rear wall being open to receive said frame of the tooth sample, the height of said side walls and the rear wall being greater than the height of said frame to provide a space for a layer of porcelain or the like.

16. The mold holder of claim 15 includes:
a support member for inserting into said cavity after the frame of the tooth sample is positioned in the mold holder to close said open side, said support member also having a height greater than the height of said frame to confine said layer of porcelain within the inner side of the support member, said rear wall and said side walls.

17. The tooth sample gripping means of claim 12 includes:
a pair of resilient arms connected together by a web at the inner ends of the arms, said arms being spread apart to receive the tooth sample therebetween and resiliently hold the sample in position.

18. The mold holder of claim 12 includes:
a pair of resilient bars connected together by a web at the inner ends of the bars, said bars being spread apart to receive the tooth sample therebetween and resiliently hold the sample in position.

19. The tooth sample of claim 12, wherein said base plate is convex on the front surface and concave on the rear surface, said incisor end of the front surface being substantially more convex than at the gingival end.

20. A color shade tooth sample comprising:
a base plate having a front surface, a rear surface, an incisor end, and a gingival end for positioning adjacent the gum line of a patient;
a pair of spaced apart feet attached to the base plate for defining a channel therebetween for receiving the support structure of an artificial tooth inside the patient's mouth;
a pair of flanges extending outward from the outer ends of the feet;
a depression formed in the outer surface of said feet to receive cooperating hump for securing the tooth sample to another object; and
a layer of porcelain or the like fused to the front surface of said base plate.

* * * * *